United States Patent [19]

Mitchell et al.

[11] 3,956,509

[45] *May 11, 1976

[54] ALCOHOL-CONTAINING DEXTRIN POWDER

[75] Inventors: William A. Mitchell, Lincoln Park, N.J.; William C. Seidel, Monsey, N.Y.

[73] Assignee: General Foods Corporation, White Plains, N.Y.

[ * ] Notice: The portion of the term of this patent subsequent to Mar. 5, 1991, has been disclaimed.

[22] Filed: Feb. 28, 1974

[21] Appl. No.: 446,879

Related U.S. Application Data

[60] Division of Ser. No. 345,143, March 26, 1973, Pat. No. 3,821,433, which is a continuation-in-part of Ser. No. 240,272, March 31, 1972, Pat. No. 3,795,747.

[52] U.S. Cl. .................................. 426/106; 426/89; 426/96; 426/103; 426/592; 426/658
[51] Int. Cl.² ..................... C12G 3/00; C12G 3/08; B65D 85/00
[58] Field of Search ............. 426/190, 191, 192, 89, 426/99, 366, 65, 213, 106, 592, 658, 96, 103; 195/31 R

[56] References Cited
UNITED STATES PATENTS

| | | | |
|---|---|---|---|
| 3,436,224 | 4/1969 | Bode | 426/191 |
| 3,615,672 | 10/1971 | Pischke | 426/366 X |
| 3,617,302 | 11/1971 | Collins | 426/99 |
| 3,619,294 | 11/1971 | Black et al. | 426/89 |
| 3,660,115 | 5/1972 | Revie | 426/65 |
| 3,663,369 | 5/1972 | Morehouse et al. | 195/31 R |
| 3,786,159 | 1/1974 | Sato et al. | 426/592 X |
| 3,795,747 | 3/1974 | Mitchell et al. | 426/192 |
| 3,821,433 | 6/1974 | Mitchell et al. | 426/192 |

*Primary Examiner*—David M. Naff
*Attorney, Agent, or Firm*—Daniel J. Donovan; Bruno P. Struzzi; Howard J. Newby

[57] ABSTRACT

Flowable dextrin powders containing about 30 to 60% ethanol sorbed therein are prepared by sorption of an aqueous alcohol solution containing about 5 to 25% moisture with expanded dextrin particulates having a bulk density of about 0.05 to 0.30 grams/cubic centimeter, a dextrose equivalent of about 5 to 15, a moisture content of about 2 to 6%, a glucose content of less than 1% and trimer, hexamer and heptamer oligomers by weight of its total oligomer content of more than 50%. The resulting products are stable when hermetically packaged and are particularly qualified as alcoholic beverage forming compositions and flavoring materials since the powders readily dissolve in cold water to form clear, low-viscosity, colorless liquids.

3 Claims, No Drawings

ALCOHOL-CONTAINING DEXTRIN POWDER

This application is a division of application Ser. No. 345,143, filed Mar. 26, 1973, now U.S. Pat. No. 3,821,433 which in turn is a continuation-in-part of application Ser. No. 240,272, filed Mar. 31, 1972, now U.S. Pat. No. 3,795,747.

BACKGROUND OF THE INVENTION

1. Field of the Invention

The present invention generally relates to alcohol-containing solids and, in particular, is directed to powders containing substantial amounts of alcohol. More specifically, the invention pertains to edible, ethanol-containing carbohydrate powders.

2. Description of the Prior Art

Prior efforts to make alcohol-containing edible powdered materials have been limited to the use of carbohydrates materials in very dry condition in order to have a significant amount of alcohol, specifically ethanol, sorbed by the dehydrated solids. For the most part, the prior art has employed carbohydrates which are either undesirably sweet or those which dissolve with considerable difficulty in cold water to produce cloudy appearing beverages. Also, because of the relatively low levels of alcohol fixation, in order to obtain effective levels of alcohol in the beverages prepared by reconstituting the prior art powders, it has been necessary to include excessive amounts of carbohydrate fixative. The presence of excess carbohydrate fixative produces beverages having too high viscosity, poor appearance and texture.

Sato, (Great Britian Pat. No. 1,138,124) discloses the use of anhydrous lactose as a medium for adsorping and/or absorbing ethanol. Sato identifies lactose anhydride as the material for combination with the ethyl alcohol to provide a stable alcohol-containing powder and implies that anhydrous alcohol must be employed in the preparation of the product since the presence of water would convert the lactose to the unacceptable hydrated crystalline form.

Bode, (U.S. Pat. No. 3,436,224) describes the preparation of an alcoholic dry beverage powder by dehydrating a vapor-sorbable particulated, starch based polysaccharide material to a moisture content of less than 0.75% and exposing the dehydrated material to anhydrous ethanol.

In both instances, it is to be noted, the prior art processes rely upon the substantially complete removal of physically or chemically combined water from the solid prior to and during the sorption of ethanol by the dehydrated solid substances. In contrast to the prior art, it has now been discovered that certain carbohydrate materials, when suitably modified with respect to physical form, will, in the presence of significant amounts of water, sorb large quantities of alcohol to form stable, flowable carbohydrate powders containing up to 60% by weight ethanol. Significantly, certain of these alcohol-containing powders will readily dissolve in cold water to form low-viscosity, clear, colorless, alcoholic solutions.

SUMMARY OF THE INVENTION

Accordingly, it is an object of the present invention to provide a flowable, high alcohol-containing powder which can be produced in the presence of substantial quantities of moisture and which, when packaged in a sealed container, is stable.

It is another object of the invention to provide a high ethanol-containing carbohydrate powder which readily dissolves in cold water to form a clear, low-viscosity, colorless liquid.

It is another object of the present invention to provide a high ethanol-containing powder which is flowable and has a minimum tendency to lump and otherwise form compacted aggregates.

It is still another object of the invention to provide a high ethanol-containing powder which can be used as a base for alcoholic beverages.

It is yet another object of the invention to provide a powder, which in addition to containing up to 60% ethyl alcohol is also amenable to the sorption of flavoring agents, particularly those usually employed in alcoholic beverages.

It is a feature of the invention that novel alcohol-containing powders are produced by utilizing the heretofore unrealized capabilities of certain modified carbohydrates to sorb large quantities of ethanol when contacted and blended with the alcohol.

Briefly stated, the objects of the invention are accomplished by bulking, i.e., increasing the bulk volume and effective surface area of specific low D.E. (dextrose equivalent) dextrins and blending the bulked dextrins with liquid ethyl alcohol in ratios such that there is sufficient dextrin present to absorb/adsorb the available ethanol and produces a dry-to-the-touch flowable powder incorporated with up to about 60% ethanol. When hermetically packaged, even though the alcohol containing powders have, in addition to 60% alcohol by weight, as much as 4.6% water, they remain chemically stable and in flowable physical condition. The products of the invention can have excellent cold water solubilities and reconstitute to provide non-sweet, low viscosity, clear colorless and sparkling liquid solutions.

The essence of the invention resides in the discovery that dextrins having low dextrose equivalent values of from about 5 D.E. to about 15 D.E. and which have been expanded to a low bulk density of from about 0.05g/cc to about 0.30g/cc have the capability for adsorbing/absorbing large amounts of alcohol. Among these dextrins are some special dextrins which are excellent film-forming materials; which can be bulked (as above) to produce low bulked density materials whose bulked physical conditions are not easily altered upon compression; and which are distinguished from the normal dextrins by having the capabilities of dissolving readily in cold water to form clear, sparkling, low viscosity and non-sweet solutions with no off-flavors. Such special dextrins have a D.P. (degree of polymerization) of from 1 to about 20 glucose units with an average D.P. of about 10 (molecular weight about 1600). Furthermore in comparison with the normal dextrins, the special dextrins, which can be produced by enzymatic hydrolysis (e.g. alpha amylase from B. Subtilis) contain about 10% less polymers in the D.P. range about 10 than the normal dextrins having the same D.E. and they have a preponderance of trimer, hexamer and heptamer content equivalent to more than 50% of the oligomers (D.P. 10 and below). Additionally, the special dextrins have only a trace to about 1% glucose and a very limited amount of maltose. The preparation of the special dextrins is discussed hereinbelow.

In summary, the low sweetness level of these special dextrins is derived from the liquid amount of glucose and maltose present, the low viscosity and good solubility and clarity is due to the reduced level of the higher D.P. materials, and the lack of off-flavors results from the use of enzymes for their preparation in contrast to the conventional acid and/or heat dextrinization. These features of the special dextrins make them particularly suitable for the purposes of the invention.

It is not known exactly why the dextrins of the invention are capable of fixing surprisingly large amounts of alcohol but it has been established that these dextrins are amorphous substances having excellent "film-forming" properties and have the inherent capability of being converted to a high bulked physical form wherein their effective surface area to unit weight ratio is exceedingly large.

The salient factors of the present invention will become apparent from the description of the preferred embodiments as set forth below.

DESCRIPTION OF THE PREFERRED EMBODIMENTS

The special dextrin substances preferred for the purposes of the present invention are prepared by special and proper alpha amylase degradation such that maltose and dextrose production are limited. Under these conditions, the D.E. is allowed to reach 5 to 10 or 15 and the dextrins contain little glucose and an irregular distribution of polymeric members with a preponderance (greater than 50%) of trimer, hexamer and heptamer polymers of glucose in the oligosaccharide range.

Briefly, the special dextrins are prepared from corn starch, tapioca starch, potato starch and other starches by the modification of these starches by alpha amylase (B. Subtilis) in accordance with the general procedures described in texts on the subject such as "Chemistry and Industry of Starch", Academic Press Inc., New York, N. Y. 1950 edited by R. W. Kerr. Importantly, the dextrinization of the starch is conducted under carefully controlled conditions of time and temperature to effect a modification of the starch such that the resulting dextrose product, when analysed by standard analytical techniques, including chromotography analysis, has a D.E. of 5 to 15 with little or no glucose and an irregular distribution of polymeric members with a preponderance (greater than 50% of trimer, hexamer and heptamer polymers of glucose in the oligosaccharide range. Although there can be small variations in the temperature range and the time to effect proper conversion, depending primarily on the type and degree of purity of the starch, the procedure normally requires maintaining the starch in aqueous suspension with the enzymes for a period of 20 to 39 minutes during which the temperature of the suspension is uniformly increased from room temperature to 65°–75°C. A detailed description of the dextrinization of a typical starch to produce a dextrin suitable for purposes of the invention is disclosed in Example I (below). Commercially, available corn syrup dextrins, typified by the products of C.P.C. International, Englewood Cliffs, N. J. under the trade name MOR-REX, have a similar functionality for purposes of the instant invention as that described above and, upon analysis have been shown to have the irregular distribution of polymeric members with a substantially similar preponderance of trimer, hexamer and heptamer polymers of glucose in the oligosaccharide range with little or no glucose present.

The dextrins, as prepared, have a bulk density of approximately 0.4–0.6g/cc and, although they have some affinity for ethyl alcohol in this physical form, a significant increase in their capabilities for adsorbing/absorbing ethyl alcohol has been found to result when they are expanded such that their bulk densities are decreased to from about 0.05g/cc to about 0.30g/cc. The procedure for bulking (expanding) the dextrins to the extent of maximizing their effective surface areas to unit weight ratios is an important operation in the practice of the process according to the invention.

Although various bulking techniques including spray drying can be employed, the preferred method for physically expanding the dextrins to a high bulk volume for enhancing their capabilities to sorb ethyl alcohol comprises forming a very thin continuous film of a water solution of the dextrin followed by drum drying the film. The bulking method can best be accomplished by drying the dextrin film from about a 50% aqueous solution of dextrin on an atmospheric drum dryer. The drum dryer roll surfaces are heated from within the drum chambers with steam at about 60 psig and the rolls are rotated at a circumferential speed of about 15 – 20 ft. per minute. These preferred conditions, of course, can be modified — the important criteria being that the dextrins should be uniformly blended with an amount of water sufficient to effect the formation of a continuous film during the drying step. The thin film of dextrin is dried to a moisture content of from about 2% to about 6% and, when doctored from the rolls forms fine particles of high bulk volume. Drum drying the dextrin material in this manner produces expanded, and not easily compressed, particles of low density, which are amorphous but crystalline-appearing materials, and which are non-hydroscopic and dissolve easily in water. After drying, the products, can be comminuted and screened, if desired, to remove particles that are either too large or too fine. The most preferred particles size fraction for practicing the invention is that which passes through a 20 mesh screen and is held on a 60 mesh screen (U.S. Standard Sieve) and has a bulk density of from about 0.10 to about 0.15 per cubic centimeter.

While it is recognized that most carbohydrate materials have the capability of sorbing relatively small amounts of ethanol, what has apparently escaped the prior art and that which forms the salient point of the present invention, is the discovery that the dextrins described hereinbefore are unique in their capabilities to sorb large quantities of ethanol to form powders which are particularly suited for forming alcoholic beverages because of their rapid and complete solubility in cold water to form water-white solutions with low viscosities. Specifically, the special dextrins are of a sufficient low average molecular weight to be readily soluble in cold water; they have excellent film-forming properties which permits them to be bulked and, are further characterized by their lack of off-flavor and sweetness.

The bulked 5, 10, and 15 D.E. special dextrins are products which exhibit rapid and complete solubility in cold water to form clear, colorless solutions. At a concentration of 40% by weight in aqueous solution, the 10 D.E. dextrin has a viscosity of about 70 centipoise at 80°F.

The special dextrins have low moisture absorption relative to the normal dextrins above 15 D.E. The 10 D.E. dextrin at 70% relative humidity and 77°F. absorbs up to about 13% moisture. While each of the bulked dextrins of the invention has excellent affinity for ethyl alcohol, the 5 D.E. dextrin has the capability of sorbing more of the alcohol, especially when some water is present and, for this reason, is the preferred carbohydrate material for the purposes of the invention.

In contrast to the prior art it is not essential to the success of the invention that anhydrous alcohol be employed for sorption by the dextrin. Surprisingly, it has been found that aqueous alcohol solutions can be sorbed to form alcohol/water-containing stable, flowable powders. While alcohol with a minimum of associated water is preferred, (primarily from the viewpoint of the desirability of having a high concentration of alcohol in the powder), ethyl alcohol having as much as 20% dissolved water can be sorbed by the bulked 5 D.E. dextrin (0.16g/cc and 4.1% moisture) to form a stable, flowable powder containing 32% ethyl alcohol, 10.5% water and 57.5% dextrin solids. If the bulked 5 D.E. dextrin has a 1 - 2% moisture content more water can be included in the alcohol solution to be sorbed. For example, a 5 D.E. dextrin at this initial low moisture content will sorb 40% by weight of an alcohol solution containing 25% water and produce a product containing 30% alcohol, 13% water and 57% dextrin solids. This is about the maximum amount of water that can be held by this dextrin. Alternatively, the bulked 5 D.E. dextrin, when contacted with 95% by weight alcohol aqueous solution will sorb sufficient solution to form a flowable powder containing 60% alcohol, 35.4% dextrin and 4.6% water.

Each of the above dextrins can be combined with ethanol to form the products of the invention by sorption of the alcohol by the dextrin in the course of a blending procedure. The addition of appropriate quantities of the alcohol to the dextrin, or vice versa, in a vessel followed by gentle, but thorough mixing, affords adequate inducement for adsorption/absorption to take place resulting in a flowable powder.

Once the alcohol-containing powdered product has been prepared it is stable for extended time periods provided it is hermetically packaged. Such packaging is necessary for stability because the product (as is the case with the prior art products) develops an ethanol vapor pressure greater than atmospheric pressure at room temperature. However, in a vapor-tight package, the product retains its alcoholic content, remains dry-to-the-touch, and retains its original flowable condition characterized by being pourable or spoonable from the container with little or no tendency to clump or otherwise aggregate. When produced for alcohol beverage purposes, each of the products can be readily tailored to contain either water soluble or ethyl alcohol soluble flavoring ingredients which are usually employed in mixed alcohol beverages. Alternatively, the products of the invention may be added to water with commercial cocktail mixes to form alcoholic beverages of excellent qualities.

In addition, the alcohol-containing powders disclosed herein can be marketed as ingredients in dry pudding and topping mixes. The alcohol content of the products is sufficiently high to ignite and support combustion and the products may be used as flaming agents for appropriate desserts. Also, the products of the invention find utility as powdered carriers for alcohol soluble flavors which would normally be degraded or lost upon drying.

The following examples illustrate the various facets of the invention. It should be understood, however, that these examples are meant to be illustrative and the invention is not to be limited thereto. In the examples which follow, "g" stands for grams, "cc" stands for cubic centimeters, "D.E." for dextrose equivalents, and the "percentages" provided are percentages by weight.

EXAMPLE I

A 0.8g quantity of alpha amylase (B. Subtilis) - (Takamine HT-1000) was dissolved in 800ml of water. Four hundred grams of potato starch was then mixed into the enzyme solution and the mixture placed in a 75°C. water bath and stirred. In approximately 8 minutes the temperature of the aqueous mixture reached 65°C. and the starch began to thicken (swell). As the temperature increased to 67°C. the enzyme activity became apparent and the slurry became less viscous. After 21 minutes and at a temperature of 71°C. the mixture was clear. The mixture was then quickly heated to the boiling point to deactivate the enzyme, then filtered, and boiling was then continued to concentrate the solution to a heavy syrup. The syrup was then vacuum dried.

The dried dextrin was determined by standard analytic technique to have a dextrose equivalent of 5, a glucose content below 1%, such a chromomatographic analysis showed an irregular distribution of the polymeric members with a preponderance (greater than 50%) of trimer, hexamer and heptamer polymers of glucose in the oligosaccharide range.

EXAMPLE II

Approximately 400g of the 5 D.E. dextrin of Example I was added to 400g of water to form a clear colorless solution. The solution was uniformly applied to the surfaces of heated drum dryer rolls. The solution formed a thin continuous film on the atmospheric drum dryer roll surfaces which were heated from within the roll chambers by steam at 60 psig. The 18 inch-diameter rolls were rotated at 3 rpm and the dried solution of dextrin was then doctored from the rolls in the form of small particles having an average bulk density of 0.16g/cc of a moisture content of 5.5%.

EXAMPLE III

A 150g amount of the bulked 5 D.E. dextrin of Example II was blended with 250g of 90% (10% by weight water) ethanol in a Hobart mixer at speed No. 2 with a wire whisk for 2 minutes. A dry-to-the-touch free flowing powder was obtained that contained 56.2% ethanol and 8.3% moisture. The bulked ethanol containing flowable powder was packaged in air-tight foil envelopes and after 6 months storage had retained its flowability characteristics and its original alcohol content.

EXAMPLE IV

A teaspoonful (3g) of the product of Example III when added to 10ml of water produced a clear, sparkling low-viscosity alcoholic solution with a non-sweet strong alcohol taste.

EXAMPLE V

A 28g quantity of the product of Example III was blended with one package (17.7g) of Holland House Daiquiri Mix to 3 ozs. of water and a small quantity of crushed ice and shaken vigorously. The resultant mixture produced a daiquiri beverage of excellent quality.

EXAMPLE VI

The procedure described in Example I was modified only to the extent of extending the time of dextrinization to produce a 10 D.E. dextrin which was then bulked (Example II) to an average density of 0.15g/cc and a moisture content of 1.5%.

EXAMPLE VII

To 275g of the bulked 15 D.E. dextrin of Example VI was added 375g of 95% ethanol (5% water by weight) and blended as in Example III. The resultant product was flowable and analyzed to contain 51.5% of ethanol and 3.3% moisture. This product, when packaged as in Example III, also retained its original physical characteristics and alcohol content after an extended storage period exceeding 6 months.

EXAMPLE VIII

To 2.8g of freeze-dried coffee was added 8.5g of the expanded ethanol containing powder of Example III to produce a flowable powdered mixture. A 175ml of hot water was added to a heaping teaspoon of the mixed powders to produce a unique coffee beverage. The beverage had excellent flavor and the alcohol content of the beverage appeared to enhance the coffee flavor notes.

EXAMPLE IX

To 40g of the bulked dextrin of Example III were added 60g of 95% alcohol containing 5cc of Firmenich liquid wine flavor (P.F.W.570039). A uniform blend of a free flowing powder was obtained. This powder was dissolved in 500ml cold water and then 500ml of cold club soda was added. A pleasant carbonated wine beverage was produced.

EXAMPLE X

A liberal quantity of the alcohol-containing powder prepared as in Example III was sprinkled over a fruit cocktail serving. The presence of the alcohol enhanced the fresh fruit flavors of the fruit flavors of the fruit cocktail.

EXAMPLE XI

A liberal quantity of the alcohol-containing dextrin prepared in Example III was sprinkled over a broiled steak and ignited. The material burned with a controlled blue flame and was then extinguished before excessive charring could take place.

By the foregoing, the present invention has been described in such detail as to enable others skilled-in-the-art to make and use the same, and, by applying current knowledge, adopt the same for use under varying conditions of service, without departing from the essential features of novelty thereof, which are intended to be defined and secured by the appended claims.

What is claimed is:

1. A comestible-containing package comprising in combination a hermetically sealed container and a flowable, dry-to-the-touch alcohol-containing powder packaged therein, said alcohol containing powder comprising:
   a. particulates of non-anhydrous expanded dextrin, said particulates of dextrin having a bulk density ranging from about 0.05 to about 0.30 grams/cubic centimeter, a dextrose equivalent of from about 5 to about 15 and further characterized by having more than 50% of the trimer, hexamer and heptamer oligomers by weight of its total oligomer (10 or less degree of polymerization) content and less than about 1% glucose, a moisture content of from about 2% to about 6% by weight, and having a particle size corresponding to a 20–60 mesh screen opening (U.S.S. Sieve), and
   b. sorbed within said dextrin particulates in an amount ranging from about 30% to about 60% by weight of said powder, an aqueous solution of ethanol containing from about 5% moisture by weight to about 25%.

2. The comestible-containing package of claim 1 further characterized in that the container is an airtight foil envelope.

3. A method of preparing a flowable, dry-to-the-touch, alcohol-containing powder which comprises:
   a. dissolving in water a dextrin having a dextrose equivalent of from about 5 to about 15 and further characterized by having more than 50 percent of the trimer, hexamer and heptamer oligomers by weight of its total oligomer (10 or less degrees of polymerization) content and less than about 1% glucose,
   b. drying the dextrin,
   c. subdividing the dried dextrin to yield particulates of dextrin having a size corresponding to a 20-60 mesh screen opening (U.S.S. Sieve), a moisture content ranging from about 2% to about 6% and a bulk density ranging from about 0.05 to about 0.30 grams/cubic centimeter, and
   d. contacting the dextrin of (c) with an aqueous solution of ethanol so as to cause the dextrin to sorb from about 30 percent to about 60% ethanol by weight of the resulting flowable ethanol-containing powder, said solution of ethanol containing from 5 to about 25% moisture by weight.

* * * * *